(12) United States Patent
Alexander

(10) Patent No.: US 7,303,391 B1
(45) Date of Patent: Dec. 4, 2007

(54) SHADE AIDE—DETERMINATION APPARATUS AND METHOD FOR DETERMINING THE DIFFERENT SHADES TO BE ADDED TO A BASE SHADE IN A PORCELAIN CROWN

(75) Inventor: Jaime Willie Alexander, Greenwood, IN (US)

(73) Assignee: Jaime Alexander, Indianapolis, IN (US)

( * ) Notice: Subject to any disclaimer, the term of this patent is extended or adjusted under 35 U.S.C. 154(b) by 0 days.

(21) Appl. No.: 11/458,685

(22) Filed: Jul. 20, 2006

(51) Int. Cl.
*A61C 19/10* (2006.01)
*A61C 19/04* (2006.01)
*A61C 13/08* (2006.01)

(52) U.S. Cl. .................. 433/26; 433/72; 433/203.1

(58) Field of Classification Search .................. 433/26, 433/72, 203.1
See application file for complete search history.

(56) References Cited

U.S. PATENT DOCUMENTS 4,620,841 A * 11/1986 Farrell et al. .................. 433/26

* cited by examiner

*Primary Examiner*—Cris Rodriguez
*Assistant Examiner*—Candice C Stokes

(57) ABSTRACT

In a shade determination apparatus for porcelain crowns a set of plastic over-tabs in different shades, sizes and specific areas of the tooth, are provided. Based on the specific base shade selected, the set of over-tabs can be tried on to any standard shade guide to achieve a more life-like appearance of the porcelain crown to match the natural teeth surrounding the crowned tooth. Different areas of the tooth such as the cervical and the incisal can be custom stained to match the natural teeth. Along with the different areas of the tooth a practitioner can determine the size of the particular area, i.e. the cervical one-third or the incisal one-half. The over-tabs can be tried on simultaneously, i.e. a cervical one-half shade can be tried on with a incisal one-half shade at the same time, thus determining a better shade match. There are also six "white striation" tabs that can fit over the other tabs at the end to determine a better match of the natural tooth.

8 Claims, 2 Drawing Sheets

SHADE AIDE—DETERMINATION APPARATUS AND METHOD FOR DETERMINING THE DIFFERENT SHADES TO BE ADDED TO A BASE SHADE IN A PORCELAIN CROWN

BACKGROUND OF THE INVENTION

The present invention relates to a shade matching apparatus for porcelain crowns that need special characteristics in shading, and also relates to a method of matching a porcelain crown to the natural teeth by relying on the human eye, and not a computer shading system of some sort.

This solution represents an advance relative to the use of any conventional shade guide. A commercial shade guide has a plurality of colors in a single uniform shade whereby no special characteristics are indicated.

Such a shade guide has limited selection options. This limitation is not due lack of options for combining different shades, but rather the fact that most natural teeth has special characteristics that would require additional staining in certain parts of a tooth. This special staining can be achieved easily by simply adding special stains to the selected base shade in a standard shade guide during the firing process. The problem with that is most dentists do not have the stain or are not trained in determining what color of stain could be used for better results.

An additional problem is that in order to achieve a more life-like appearance by adding special stains a dentist is usually limited to the options available. A practitioner would either have to send the patient to the lab, which is usually inconvenient for the patient, or the lab might come to the dentist office, which is usually inconvenient for the lab as well as the dentist.

Another option for shading is a computerized shading system of some sort, and these systems have limitations that usually produce an unsatisfactory result. Although a computerized system can and usually finds different shades in a tooth, they are programmed to select said different shades from the colors in a standard shade guide. For example, if a natural tooth has a chroma shade at the cervical or a translucent shade at the incisal the computer will pick a shade from the conventional shade guide that is the closest match to that. A standard shade guide does not include shades that are translucent or chromatic, therefore the shade selected likely will not match correctly.

Another problem is that with a computerized system a practitioner or libratory technician places the handpiece of the system directly against the tooth, and the computer can not take into account the different factors that may need to be noted in determining the shade, such as a persons skin tone or the shape, size and color of the patients lips, which sometimes play a big part in determining the shade of an anterior tooth.

BRIEF SUMMARY OF THE INVENTION

The invention relates to a shade determination apparatus for improving the shade matching abilities of porcelain crowns to the natural teeth by selecting the different shades, chromas, hues and translucencies in the different portions of the existing natural teeth, and then conveying these specifications to the libratory in a concise and clear way.

The present method is used for determining what stain or stains may need to be added to the porcelain shade of a standard shade guide to achieve a more life-like appearance of a porcelain crown to the natural teeth. This method includes the steps of: after choosing a base porcelain shade for a crown, if additional shading is needed then using the provided stain tabs selecting a cervical stain and/or an incisal stain that matches the patients natural teeth; then using the provided stain tabs choosing the how much of the cervical or incisal need the stain; if other characteristics are needed, using the white striation over-lays to determine what size or direction the striations should be.

The stain tabs fit over most standard shade guides so that the cervical stain can actually be tried on the cervical of the shade tab tooth, and the incisal can be tried on the incisal of the shade tab tooth allowing for a more accurate match. For each color of stain there are three different sizes to choose from, allowing the practitioner to choose how much of the cervical or incisal of the tooth needs the stain. In addition, the stain tabs can be tried on together so the dentist can see what a cervical stain and an incisal stain look like together on the selected base shade, allowing for more concise match to natural teeth. The stain tabs rotate halfway around so that once placed on a shade tab the stain can be rotated with the shade tab for easier access to either maxillary or mandibular teeth.

Once the desired shade and any additional stain are selected then the practitioner has an exact map for the libratory to insure no miscommunication in the process of achieving a life-like appearance of a porcelain crown and the matching of this crown to the natural teeth.

DETAILED DESCRIPTION OF THE INVENTION

As used herein, the term "stain tab" refers to the current invention, and the term "shade tab" refers to any standard commercial shade guide tab.

Figure 1:
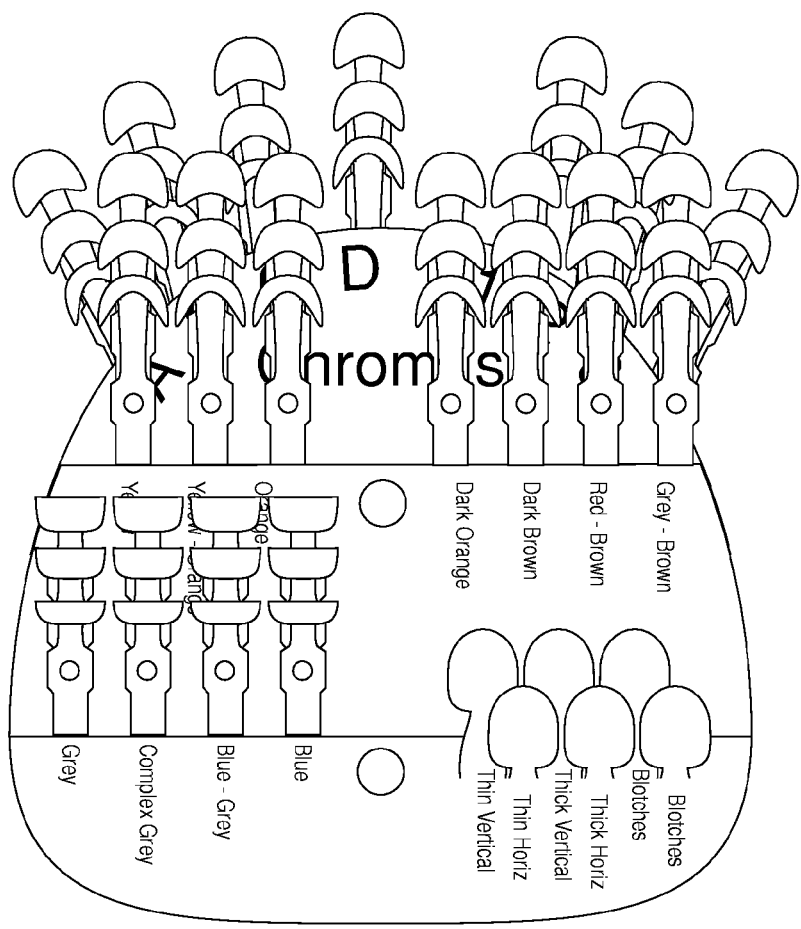
FIG. 1 is an illustration of the entire apparatus with stain tabs placed in the holder.

As seen in FIG. 1, the present invention provides a holder shaped like that of a central incisor, whereas the stain tabs can be placed in an organized fashion such as cervical shades located in the cervical portion of the holder, and incisal shades located in the incisal portion of the holder. The separate sections of the holder will also rotate around for easier access to the desired portion of the stain guide. Therefore if you are trying to find a cervical shade you can rotate the top portion of the holder to expose only those shades and the others are not in the way, thus eliminating any distraction of the other shades, but still having all the shades available in one holder. As well as being able to rotate and separate the different shades, once a certain shade is chosen each individual set of stain tabs can be removed from the holder to be tried on to the base selected shade tab.

Figure 2:
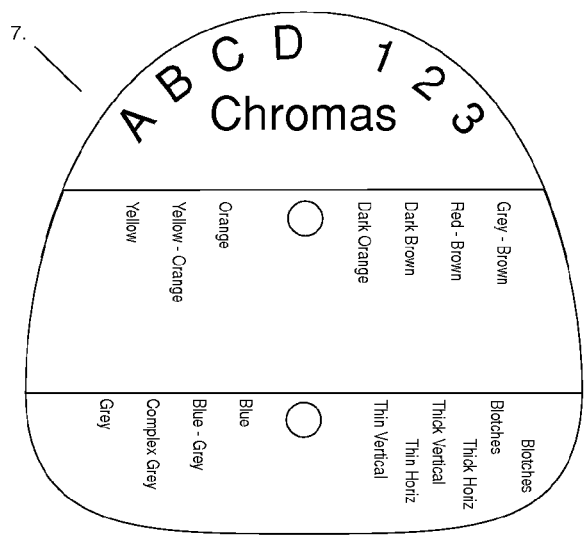
FIG. 2 illustrates the holder without the tabs but the different colors available.

The apparatus and method of shade matching has been simplified by separating the different sections of a tooth to correspond with the different sections of the stain tab holder. The different stains have then been clearly labeled 7 as seen in FIG. 2. Although the stains have been chosen based on my experience with staining crowns, the shades are subject to change or addition.

Surprisingly, the present inventive measures make it possible to obtain a more life-like appearance than that of a computerized system. In creating the present invention and testing it in a clinical setting, I have also found that in some instances a standard shade guide or base shade is not available that would come close to the natural tooth shade, but using the present invention a base shade was able to be obtained by choosing from the stain shades. An example of such an instance would be when a patient natural tooth is too grey or yellow or brown to even come close to any standard shade guide shade. In which a stain shade was chosen as the base shade and then adding any other customized characteristics.

Figure 3:
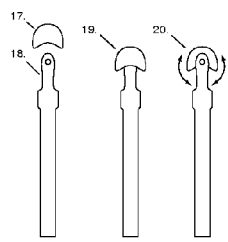
FIG. 3 illustrates the cervical one-half stain tab.

FIG. 3 illustrates the one-half 17 cervical plastic stain tab. The plastic handle 18 is then attached with a small plastic eyelet on the back of the stain tab. When creating the stain tabs a separating agent was used to allow the stain tab to fit over the attachment of a standard shade guide, so that the stain tab would fit over the top of a shade tab and hug the cervical of that shade tab for better visual analysis. When trying on the stain tab the handle to the stain tab would be held against the back of the shade tab. The purpose of using a small plastic eyelet to attach the handle to the stain tab was to allow the stain tab to rotate half-way around to accommodate a standard shade guide that also rotates around for easier access to maxillary or mandibular teeth 20.

Figure 4:
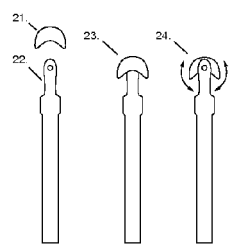
FIG. 4 illustrates the cervical one-third stain tab.

FIG. 4 illustrates the one-third 21 cervical plastic stain tab. The plastic handle 22 is then attached with a small plastic eyelet on the back of the stain tab. When creating the stain tabs a separating agent was used to allow the stain tab to fit over the attachment of a standard shade guide, so that the stain tab would fit over the top of a shade tab and hug the cervical of that shade tab for better visual analysis. When trying on the stain tab the handle to the stain tab would be held against the back of the shade tab. The purpose of using a small plastic eyelet to attach the handle to the stain tab was to allow the stain tab to rotate half-way around to accommodate a standard shade guide that also rotates around for easier access to maxillary or mandibular teeth 24.

Figure 5:
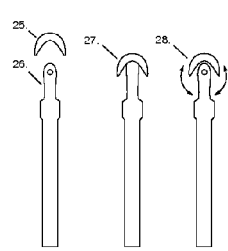
FIG. 5 illustrates the cervical one-forth stain tab.

FIG. 5 illustrates the one-forth 25 cervical plastic stain tab. The plastic handle 26 is then attached with a small plastic eyelet on the back of the stain tab. When creating the stain tabs a separating agent was used to allow the stain tab to fit over the attachment of a standard shade guide, so that the stain tab would fit over the top of a shade tab and hug the cervical of that shade tab for better visual analysis. When trying on the stain tab the handle to the stain tab would be held against the back of the shade tab to rotate half-way around to accommodate a standard shade guide that also rotates around for easier access to maxillary and mandibular teeth 28.

Figure 9:
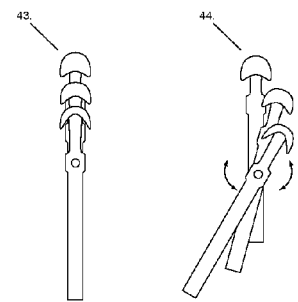
FIG. 9 illustrates a cervical stain tab of one color with the three different sizes, and how it rotates and folds back up.

In accordance with the invention, it is advantageous for the three sizes of each stain be easily accessible, therefore, I found it to be best utilized by attaching all three sizes together starting with the one-half on the bottom, then stacking the one-third on top of that and ⅛th of an inch below it, finally stacking the one-forth on top of that and ⅛th of an inch below it. Then attaching all three together with a plastic eyelet 43. Again the plastic eyelet allowing for rotation outward to expose the desired size 44, and then folding all three stain tabs back up as seen in FIG. 9.

Figure 6:
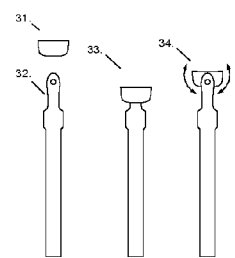
FIG. 6 illustrates the incisal one-half stain tab.

FIG. 6 illustrates the one-half 31 incisal plastic stain tab. The plastic handle 32 is then attached with a small plastic eyelet in the back of the stain tab. When creating the stain tabs the eyelet was created to be flat so that the stain tab can fit up under the incisal edge of the shade tab and hug the incisal edge of that shade tab for better visual analysis. When trying on the stain tab the handle to the stain tab would be held against the front of the shade tab. The stain tab would also be able to rotate half-way around to accommodate a standard shade guide that also rotates around for easier access to maxillary and mandibular teeth 34.

Figure 7:
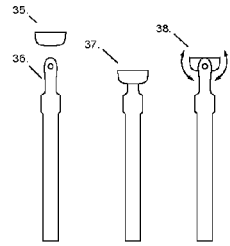
FIG. 7 illustrates the incisal one-third stain tab.

FIG. 7 illustrates the one-third 35 incisal plastic stain tab. The plastic handle 36 is then attached with a small plastic eyelet in the back of the stain tab. When creating the stain tabs the eyelet was created to be flat so that the stain tab can fit up under the incisal edge of the shade tab and hug the incisal edge of that shade tab for better visual analysis. When trying on the stain tab the handle to the stain tab would be held against the front of the shade tab. The stain tab would also be able to rotate half-way around to accommodate a standard shade guide that also rotates around for easier access to maxillary and mandibular teeth 38.

Figure 8:
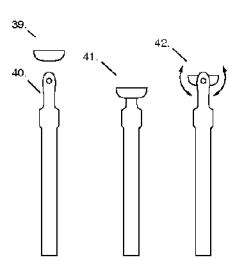
FIG. 8 illustrates the incisal one-forth stain tab.

FIG. 8 illustrates the one-forth 39 incisal plastic stain tab. The plastic handle 40 is then attached with a small plastic eyelet in the back of the stain tab. When creating the stain tabs the eyelet was created to be flat so that the stain tab can fit up under the incisal edge of the shade tab and hug the incisal edge of that a shade tab for better visual analysis. When trying on the stain tab the handle to the stain tab would be held against the front of the shade tab. The stain tab would also be able to rotate half-way around to accommodate a standard shade guide that also rotates around for easier access to maxillary and mandibular 42.

Figure 10:
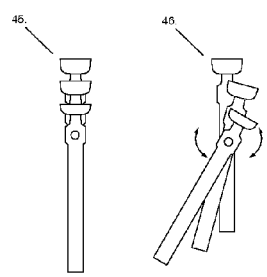
FIG. 10 illustrates an incisal stain tab of one color with the three different sizes, and how it rotates and folds back up.

In accordance with the invention, it is advantageous for the three sizes of each stain be easily accessible, therefore, I found it to be best utilized by attaching all three sizes together starting with the one-half on the bottom, then stacking the one-third on top of that and ⅛th of an inch below it, finally stacking the one-forth on top of that and ⅛th of an inch below it. Then attaching all three together with a plastic eyelet 45. Again the plastic eyelet allowing for rotation outward to expose the desired size 46, and then folding all three stain tabs back up as seen in FIG. 10.

Figure 11:
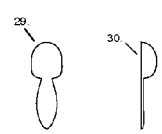
FIG. 11 is a perspective front and side view of the white striation overlays.

As previously discussed a natural tooth can have several different characteristics in the cervical or incisal, but as well as those differences, a natural tooth can have white opacities or white striations. In accordance with the invention there are also tabs provided for such instances. Once a base shade and any cervical or incisal stains are chosen sometimes in order to create a more life-like appearance white striations need to be added. Since the design of the stain tabs is such that a cervical stain can be tried on with an incisal stain simultaneously, I have also created an overlay FIG. 11 for white striations of different sizes, shapes and direction that fit over the top of the stain tabs. Whether that be incisal alone or cervical alone or both together. The overlay may be the finishing touch to create the best shade match available. 29 is a front view of the overlay. 30 is a side view of the overlay showing the convexity of the tab, and illustrating the ability to fit over the entire shade tab with stain tabs in place.

With all the information available within the present invention, the doctor or operator can convey to the libratory the exact shade, customization, or any other special instructions desired when shade matching a porcelain crown to the natural teeth thus decreasing the amount of chair time needed for the patient, and eliminating any traveling of either patient to libratory or libratory to practitioner's office.

The present invention has a further advantage in that it can be used as a teaching tool to learn to recognize certain hues, chromas, translucencies, or opacities. The more you use the present invention the quicker you are to recognize certain characteristics, or range of colors.

What is claimed is:

1. A method for determining the custom shade of a porcelain crown thereof, which comprises the steps of:
    selecting a base shade from any standard shade guide and then using a provided over-tab or stain tab determining if a different shade is needed in the cervical portion of the crown;
    selecting a base shade from any standard shade guide and then using the provided over-tabs or stain tabs determining if a different shade is needed in the incisal portion of the crown;
    if a different shade is needed in the cervical, using the provided over-tabs or stain tabs to determine how much of the cervical needs the selected shade;
    if a different shade is needed in the incisal, using the provided over-tabs or stain tabs to determine how much of the incisal needs the selected shade;
    after determining any shade alterations in the cervical or the incisal, using the provided over-tabs or white striations tab to determine any striations needed in the crown; and
    if any striations are needed, using the provided over-tabs or striation tabs to determine what type of striation is desired.

2. The method of claim 1 wherein the stain tabs can be fitted over any standard shade guide.

3. The method of claim 2 an incisal stain tab can be tried on at the same time as a cervical stain tab.

4. The method of claim 3 wherein a striation tab can be tried on and fit over the top of an incisal stain tab and a cervical stain tab simultaneously.

5. The method of claim 1 wherein after a matching stain tab is selected for the cervical portion of a crown, then the operator has three options to choose from on that stain tab to determine how much of the cervical portion needs the selected shade;
    wherein the three options being the cervical one-forth, the cervical one-third and the cervical one-half.

6. The method of claim 1 wherein after a matching stain tab is selected for the incisal portion of a crown, then the operator has three options to choose from on that stain tab to determine how much of the incisal needs the selected shade;
    wherein the three options being the incisal one-forth, the incisal one-third and the incisal one-half.

7. The method of claim 2 wherein the stain tabs rotate half way around in both directions, making it easily accessible to both the maxillary and the mandibular.

8. The method of claim 1 further comprising the steps of:
    after all the selected stain tabs are determined the operator relaying to the laboratory the exact specifications for the custom shade;
    thereby eliminating the need for the patient to travel to the laboratory and eliminating the need for the laboratory to travel to practioner's office;
    recording the base shade chosen from any standard shade guide, then recording what color of any additional stain is needed in the cervical and/or incisal portions;
    then recording what portion of the cervical and/or incisal would need the stain; and
    recording if any white striations are needed and the amount or direction of the striations.

* * * * *